United States Patent
Camp et al.

(10) Patent No.: US 9,659,505 B2
(45) Date of Patent: May 23, 2017

(54) DEMENTIA THERAPY METHOD AND INSTRUMENT

(71) Applicants: Cameron J. Camp, Solon, OH (US); Vincent Antenucci, Streetsboro, OH (US); Linda M. Camp, Solon, OH (US); Karen Bescan, Grafton, OH (US); Evan Bescan, Grafton, OH (US); Charles A. Nelson, Akron, OH (US); John C. Ryder, Chippewa Lake, OH (US)

(72) Inventors: Cameron J. Camp, Solon, OH (US); Vincent Antenucci, Streetsboro, OH (US); Linda M. Camp, Solon, OH (US); Karen Bescan, Grafton, OH (US); Evan Bescan, Grafton, OH (US); Charles A. Nelson, Akron, OH (US); John C. Ryder, Chippewa Lake, OH (US)

( * ) Notice: Subject to any disclaimer, the term of this patent is extended or adjusted under 35 U.S.C. 154(b) by 0 days.

(21) Appl. No.: 14/813,094

(22) Filed: Jul. 29, 2015

(65) Prior Publication Data

US 2016/0035240 A1 Feb. 4, 2016

Related U.S. Application Data

(60) Provisional application No. 62/030,081, filed on Jul. 29, 2014.

(51) Int. Cl.
*G09B 15/00* (2006.01)
*A61B 5/00* (2006.01)

(52) U.S. Cl.
CPC ............ *G09B 15/00* (2013.01); *A61B 5/4088* (2013.01)

(58) Field of Classification Search
CPC .... G09B 15/00; G09B 15/023; G09B 15/002; G09B 15/003; G09B 5/06; G09B 15/004; G09B 19/00; G09B 7/00
USPC ........................................................ 84/47 R
See application file for complete search history.

(56) References Cited

U.S. PATENT DOCUMENTS

2005/0005761 A1* 1/2005 Knudsen ................ G09B 15/08
84/645

* cited by examiner

*Primary Examiner* — Kimberly Lockett
(74) *Attorney, Agent, or Firm* — D. A. Stauffer

(57) ABSTRACT

A dementia therapy method that involves PWD in playing music, particularly as part of an ensemble "performing in concert", which provides a rewarding and encouraging result of utilizing abilities that they may not even know they had to produce pleasing music. This method utilizes musical instruments adapted for playing by PWD who can utilize procedural rather than declarative memory in playing. By connecting a plurality of the instruments to a central director's console the combined musical sound can be coordinated to make it pleasing. Then several PWD are trained to play components of songs together as an group. An example of our specially adapted musical instruments is an easily played percussion instrument having an organized layout of one or more tone bars that, when struck (or touched) by a player generate a musical tone. The instrument may be further adapted to ease its use by movement restricted players.

13 Claims, 2 Drawing Sheets

DEMENTIA THERAPY METHOD AND INSTRUMENT

CROSS-REFERENCE TO RELATED APPLICATIONS

This application claims the benefit of U.S. Provisional Patent Application No. 62/030,081 filed Jul. 29, 2014, said application hereby incorporated in its entirety by reference herein.

BACKGROUND OF THE INVENTION

One of the major obstacles facing Person(s) With Dementia (abbreviated PWD herein) and their caregivers is the stigma associated with this condition, plus the sense of hopelessness regarding the prospects of rehabilitation efforts. Commonly held beliefs about dementia include the idea that PWD cannot learn new information or acquire new skills, and so no attempts are made to teach them anything. Worse yet is the assumption that since there doesn't appear to be a "cure" for dementia, especially for the Alzheimer's version, then there is no point in attempting rehabilitative therapy. Such beliefs inhibit development of effective non-pharmacologic treatments for PWD, as well as the willingness of caregivers and PWD themselves to initiate such treatments. Similar issues are at play when dealing with other kinds of cognitive disabilities.

Thus it is an object of the present invention to provide a therapeutic method for persons with cognitive disabilities, especially those with more severe forms of it such as dementia (including Alzheimer's dementia).

BRIEF SUMMARY OF THE INVENTION

The applicants believe that suitable therapy can at least improve quality of life for persons with cognitive disabilities, and depending upon the degree and degradation rate of a cognitive disability a measure of rehabilitation and/or stabilization may be possible. In particular we induce learning as a means of therapy. To this end we have developed our system of a therapy method combined with musical instruments adapted for implementing the method. This method utilizes musical instruments adapted for playing by PWD who can utilize procedural rather than declarative memory in playing. Learning music using procedural memory is rewarding and thus therapeutic because it can be accomplished without relying on deteriorating cognitive abilities.

Group therapy is enhanced by connecting a number of the instruments to a central director's console whereby the combined musical sound of the group can be coordinated to make it pleasing. An example of our specially adapted musical instruments is an easily played percussion instrument having an organized layout of one or more tone bars that, when struck (or touched) by a player generate a musical tone. The instrument may be further adapted to ease its use by movement restricted players.

Our method is a regimen for training persons with dementia to play components of songs together so that they may perform as an ensemble in concert. Our purpose has been to demonstrate the capacity of such persons to learn, and to demonstrate this capacity in a manner that is meaningful to participants. In addition, viewing such a performance has a powerful impact on observers and serves to counteract negative stereotyping for them as well as PWD themselves.

Other objects, features and advantages of the invention will become apparent in light of the following description thereof.

BRIEF DESCRIPTION OF THE DRAWINGS

Reference will be made in detail to preferred embodiments of the invention, examples of which are illustrated in the accompanying drawing figures. The figures are intended to be illustrative, not limiting. Although the invention is generally described in the context of these preferred embodiments, it should be understood that it is not intended to limit the spirit and scope of the invention to these particular embodiments.

Certain elements in selected ones of the drawings may be illustrated not-to-scale, for illustrative clarity. The cross-sectional views, if any, presented herein may be in the form of "slices", or "near-sighted" cross-sectional views, omitting certain background lines which would otherwise be visible in a true cross-sectional view, for illustrative clarity.

Elements of the figures can be numbered such that similar (including identical) elements may be referred to with similar numbers in a single drawing. For example, each of a plurality of elements collectively referred to as 199 may be referred to individually as 199*a*, 199*b*, 199*c*, etc. Or, related but modified elements may have the same number but are distinguished by primes.

For example, 109, 109', and 109" are three different versions of an element 109 which are similar or related in some way but are separately referenced for the purpose of describing modifications to the parent element (109). Such relationships, if any, between similar elements in the same or different figures will become apparent throughout the specification, including, if applicable, in the claims and abstract.

Figure 1:
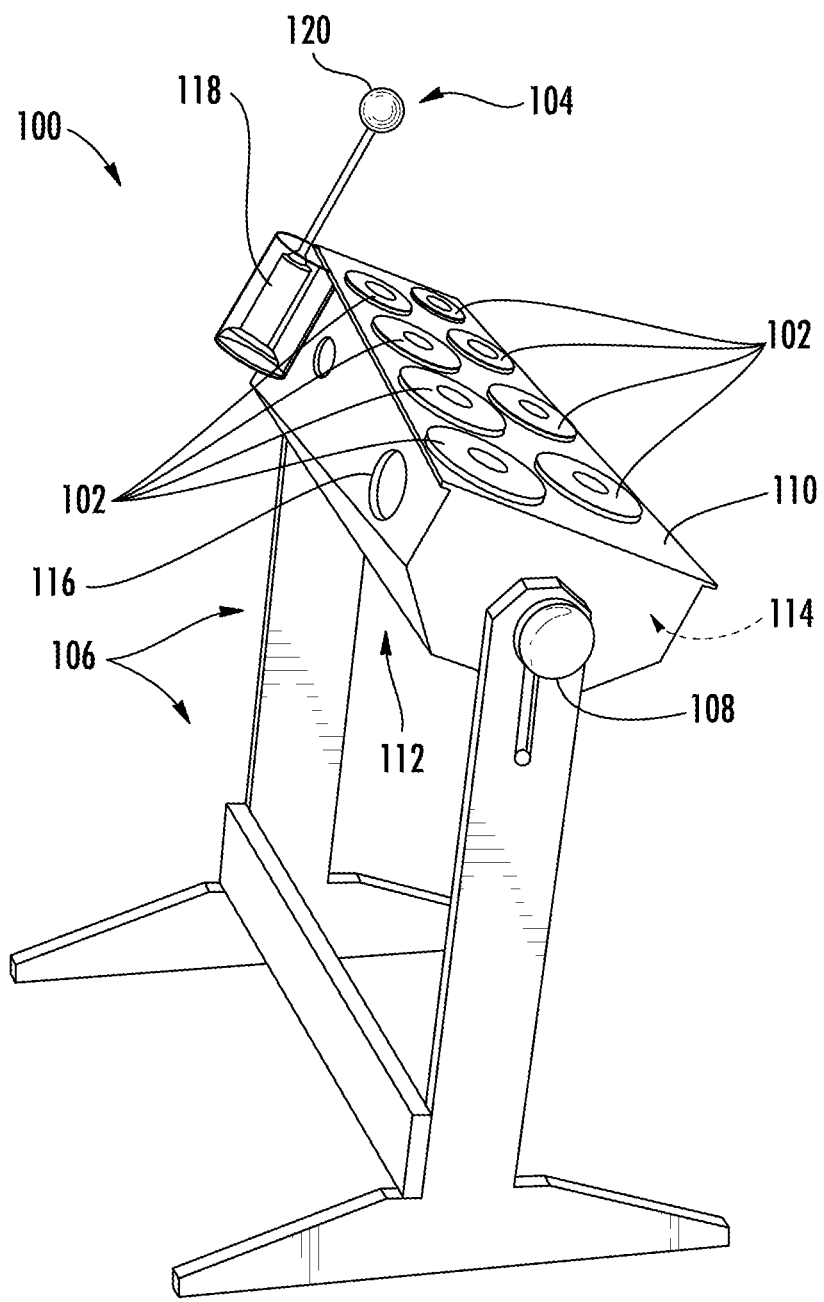

The structure, operation, and advantages of the present preferred embodiment of the invention will become further apparent upon consideration of the following description taken in conjunction with the accompanying drawings, wherein:

FIG. 1 is a perspective view of a therapeutic instrument according to the invention.

Figure 2:
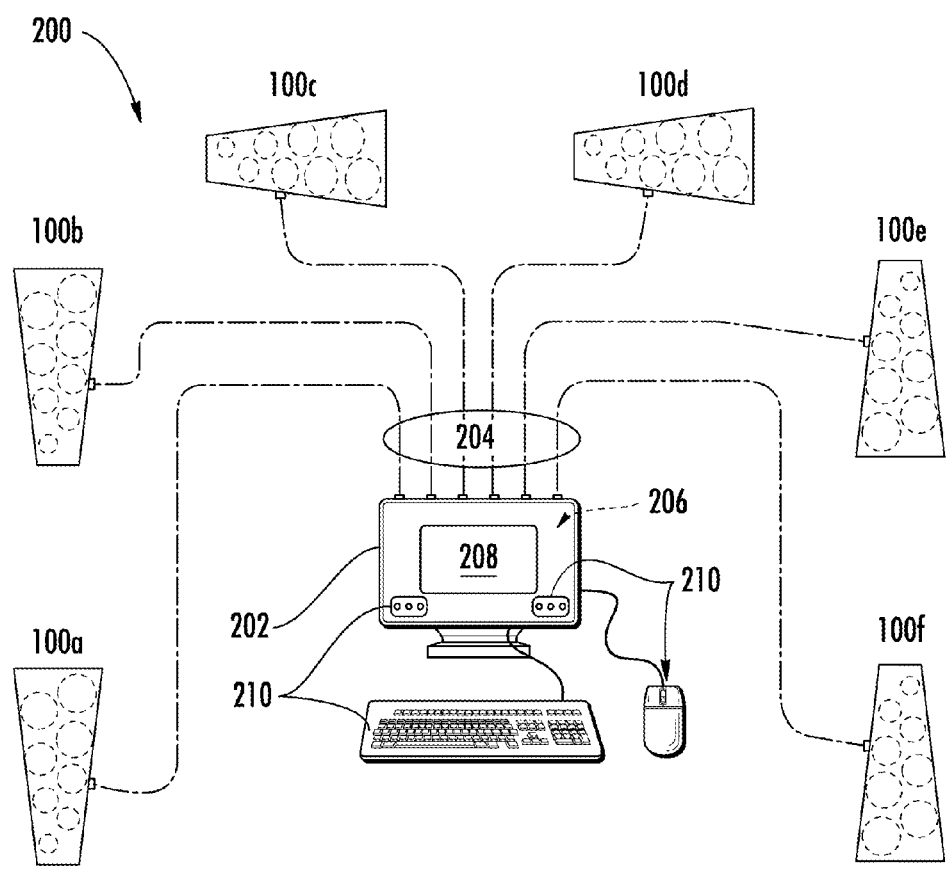

FIG. 2 is a schematic overview of a system for implementing a therapeutic method according to the invention.

DETAILED DESCRIPTION OF THE INVENTION

The following table is a glossary of terms and definitions, particularly listing drawing reference numbers or symbols and associated names of elements, features and aspects of the invention(s) disclosed herein.

| REF. | TERMS AND DEFINITIONS |
|---|---|
| 100 | Therapeutic instrument (e.g., a "Kaevaphone") |
| 102 | tone bar |
| 104 | mallet, "wand" |
| 106 | instrument stand |
| 108 | hand knob |
| 110 | playing surface |
| 112 | body |
| 114 | electronics of instrument e.g., CPU, tone generator, bar lighting controller, etc. |
| 116 | speaker |
| 118 | wand grip/handle |
| 120 | wand mallet head (bulb) |

-continued

| REF. | TERMS AND DEFINITIONS |
|---|---|
| 200 | System of therapeutic instruments (100a . . . 100f) - collectively referenced as instruments 100. Ensemble of instrument players with a director - for implementing a therapeutic method in a group activity conducted by a director/therapist. |
| 202 | Director's console (control panel) |
| 204 | Cables connecting the instruments 100 to the console 202 |
| 206 | console processor/software |
| 208 | touch screen/display |
| 210 | control buttons and/or keyboard and/or mouse |

The invention(s) will now be described with reference to the drawings using the reference numbers and symbols listed in the above table.

The issues noted above in the background section were highlighted in a recent conference called in December, 2013, by AARP in Washington, D.C. The title of the conference was "Living Well With Dementia." This reflects a desire to combat stigma and sense of helplessness so that persons with dementia (PWD), and their loved ones may have improved quality of life.

The inventors believe that this is made possible by a paradigm shift in which dementia is viewed as a disability rather than a disease process. In this way, caregivers are able to address challenging (negative) PWD behaviors and to effect a good quality of life. Thus "interventions" that are used for persons with physical disabilities can be used as a model for treatment of persons with dementia (a cognitive disability). It also is important to remember that the time that PWD spend in engaging, meaningful activity is inversely related to the time that they will be exhibiting challenging behaviors. Therefor it is important to develop engaging activity as a means of providing non-pharmacologic treatment for persons with dementia, and in so doing to challenge stigma associated with dementia.

By viewing dementia as a cognitive disability, the applicants concluded that an effective method for dealing with dementia involves two aspects of disability therapy/treatment:
 1. circumvention of deficits, and
 2. focusing on making best possible use of remaining capability.
Our approach for implementing such aspects of therapy is to:
 1. Avoid reliance on declarative memory/standard learning procedures, and
 2. Use relatively preserved capabilities in persons with Alzheimer's disease, i.e., procedural functions such as motor learning.

Therefor we have developed a therapy method that involves PWD in playing music, particularly as part of an ensemble "performing in concert"—this we find to be very engaging for PWD because of the rewarding and encouraging result of utilizing abilities that they may not even know they had to produce a pleasing musical result. At the present we are calling our method the MusicMuse™ method (which we intend to trademark if made public). The present disclosure uses this name to refer to the present invention, but it should be considered no more limiting than a more generic term for what is disclosed herein.

In order to implement our method we have developed suitable apparatus, i.e., specially adapted musical instruments 100. Referring to FIG. 1, an embodiment of our instrument 100 is an easily played percussion instrument having an organized layout of one or more tone bars 102 that, when struck (or touched) by a player generate a musical tone. The tone bars 102 may be as simple as xylophone bars, but preferably work in a similar fashion as an "Orff instrument", and more preferably are electronic triggers for sound generators such as the electronically driven speaker(s) of an electronic keyboard. In a further development, our instrument (device) is adapted to ease its use by elderly and/or movement restricted players. At the present we are calling our instrument a Kaevaphone™ (which we intend to trademark if made public). The present disclosure uses this name to refer to the instrument/device 100 aspect of the present invention, but it should not be considered as limiting to just the exemplary embodiment that is disclosed herein.

In brief summary, the invention focuses on procedural/nondeclarative/implicit memory such as:
 Habits
 Skills
 Motor Learning
 Location Learning
 Conditioning
 Priming Our method is an adaptation and specialized implementation of methods first developed by Maria Montessori (the Montessori program/method) which makes extensive use of manipulatives and external aids for teaching in a way that results in what she terms "Unconscious Learning". We selected the Montessori method as a platform for our method of therapy or rehabilitation because of parallel objectives. In particular, we noted the following actions as being closely aligned with our method actions:
 Circumvent deficits
 Allow independent functioning
 Engage in meaningful activity
 Provide feedback and success
 Enhance self-esteem
 Enable functioning at highest possible level
 Provide meaningful social roles
Thus our method inventively builds on Montessori-based tasks that:
 PROVIDE:
  structure and order
  immediate feedback
  high probability of success
  repetition
  task break down and which
 UTILIZE PROCEDURAL MEMORY particularly of the following types:
  skills
  habits
  motor learning
  repetition priming Within the framework described hereinabove we have developed our "System Of Instruments And Therapy Method." (MusicMuse™). This has involved devising a regimen for training persons with dementia to play components of songs together so that they may perform as an ensemble in concert. Our purpose has been to demonstrate the capacity of such persons to learn, and to demonstrate this capacity in a manner that is meaningful to participants. In addition, viewing such a performance has a powerful impact on observers and serves to counteract negative stereotyping for them as well as PWD themselves.

In this regard, we worked from Squire's (1994) model of memory, in which he describes relatively preserved capacities in persons with Alzheimer's disease, such as motor learning (procedural memory/learning). We wanted to work with a music learning and performance system that would utilize existing capacities of PWD and that had shown benefit in populations with disabilities. Thus, we utilized Orff-like musical instruments such as wooden xylophones and metallophones, teaching methods adapted for such instruments such as the Kodaly method of teaching music, along with techniques from neuropsychological rehabilitation such as "errorless learning" (e.g., taking off any bars of notes that would not be played in performing a song), extensive use of external cueing, etc.

Training is conducted in graduated steps according to ability, such as starting with touching bars 102 with hands, running hands over bars, holding a mallet 104, running the mallet over bars, using one mallet with a steady beat, one mallet with a repeated pattern between two bars, two mallets with a steady beat, etc. This approach allows determination of which level of ability each individual with dementia can master, and to fit suitable specific pieces of a song's components to individuals. Doing this, we enabled 12 persons with dementia to perform a song (Don't Fence Me In) in concert, with each person being able to contribute in a satisfying way.

In the course of the development of this system we found that the use of standard Orff instruments could present challenges to older adults with dementia because they are likely to have varying degrees of physical limitations. We therefore began to consider what would be more ideal as musical instruments for work with dementia populations. That has led to the development of a new type of instrument 100 specifically for use by persons with dementia—the Kaevaphone™. Such an instrument 100 plus our corresponding MusicMuse™ training method could be used by activity staff, music therapists, and other caregivers to train persons with dementia to play a musical instrument, either individually or in concert with others. For example, we envision concerts where PWD would perform together and with family members, children, staff members, etc. In addition, it could serve as a powerful means of combating stigma associated with dementia. Finally, such an instrument 100 could be used with other populations of persons with disabilities, as well as the non-disabled.

An Instrument For Implementing The Method

FIG. 1 is a perspective view of the Kaevaphone instrument 100, including a stand.

FIG. 2 shows a schematic of the Director's Console 202 with a connected ensemble of six instruments 100 (100a . . . 100f).

The Instrument

Note that the illustration in FIG. 1 implies that this is an acoustic percussion device like a xylophone, but as discussed further below, a more useful embodiment of our instrument 100 is one based on electronic music (tone/sound) generation.

Stand

The instrument stand 106 as shown in FIG. 1 is simple and made of, for example, ¾"×4" wooden boards, although many other materials will obviously also work well.

The Stand 106 is designed so that it will be usable by a player either seated or standing (the instrument should be at about waist height for a typical standing player).

By loosening then tightening the two Hand-Knobs 108 (one shown), a person can easily adjust both the height and the tilt-angle of the instrument playing surface 110 to suit the comfort of the player. In particular, we feel it is important to allow tilt anywhere between horizontal and vertical on at least one side of the stand, because it is easiest to play if the tone bars 102 can be hit by a mallet 104 in-hand when the player's arm is in a comfortable position, which means that the required movement is mostly of the forearm and/or wrist. The thing to particularly avoid is requiring raised, unsupported upper arms.

Instrument Body

The main body 112 of the instrument is a so-called "Sound Box" (however it is not limited to an acoustic instrument, as mentioned above). With or without acoustic properties, the body 112 may simply provide a structure for holding the playing surface 110 with tone bar 102 in position. As such it provides means of attaching the playing part of the instrument 100 (preferably adjustably) on to a supporting stand 106. On its top playing surface 110 the "Tone-Bars" 102 are mounted (e.g., eight of them). The tone bars 102 are illustrated as round disks and correspond to, for example, the eight tones in a scale, not including the five accidental (sharp/flat) tones. This configuration is only one of many possible embodiments of our instrument.

The instrument body 112 is fabricated of, for example, light plywood, but many materials and shapes can be considered. As shown it is about 24 inches long and 6 inches deep.

Tone Bars

Key elements of the Kaevaphone are the Tone Bars 102. When struck by the Player using his/her "Wand" (mallet) 104, the Tone Bar 102 generates a tone or musical note. By having several Tone Bars, the Player can generate many notes and thus many tunes as described further below.

An electronic based Kaevaphone can offer more flexibility and variety of sound, so the Tone Bars of this embodiment are preferably electronic in nature. There are existing devices (e.g., electronic drum pads) that generate an electrical pulse when struck. These could be the basis for the design of our Tone Bars 102.

On-Board Electronics

In FIG. 1, the Bars 102 are shown as round in shape since they would be easier to strike (being a larger target!). In the "Learning Mode" as described below, each Bar 102 can be lighted in sequence to indicate to the Player that it should be the next Bar in the Tune to be struck. To accomplish this, there may be electronics 114 in, or associated with an instrument 100, e.g., a CPU, tone generator, bar lighting controller, etc. Further, the electronics 114 can be programmed to cause the tone bars 102 to produce a variety or range of tones/sounds, to fit the tunes being played by a group 200 of instruments 100.

For example, the electronics 114 may be a small dedicated digital Processor with its custom designed software. The Processor will sense which Bar 102 has been struck and generate a corresponding tone to speakers 116; preferably at least one in front and one in back of the Sound Box/body 112.

The Processor 114 can assign each Tone Bar 102 its tone to be sounded when it is struck. Therefore when an Ensemble 200 of Kaevaphones 100 (100a . . . 100f) come together, each can be playing in a different range of notes, or each can be sounding as a different instrument. Thus a Kaevaphone can be thought of as a specialized type of synthesizer.

For safety sake, each "Kaevaphone" can have a rechargeable battery or low voltage power supply cord rather than be connected to 110 volt AC. A connecting cable 204 plugged into a USB port or the like on the back of the Sound Box 112 can serve to recharge a battery, or to provide low voltage power, and also may be used as a data link 204 to a Director's Console 202 described further below.

Wand

The Player would hold in his/her hand a "Wand" 104 which he/she would use to strike each Tone Bar 102 to generate the desired music.

As illustrated in FIG. 1, the Wand 104 is shaped with a relatively large diameter grip 118 so to be easier to handle. The Wand 104 could be made of wood or a durable plastic to be light and strong, and has a mallet head (Bulb) 120 at the end, as do existing musical mallets. The head 120 is as soft as possible while retaining a suitable weight, resilience and/or firmness as determined by ordinary designer-developers of similar electronic percussive instruments.

Director's Console

FIG. 2 shows a schematic of a director's console (control panel) 202 with an ensemble 200 of six instruments (Kaevaphones) 100. This is an example of enhancing the therapeutic method by integrating instruments and players into a therapy group 200 interactively directed by a therapist using a control panel 202. As shown, a grouping of instruments 100 (with players) can be advantageously interconnected by cables 204 to form an ensemble 200 where a control panel 202 is positioned in the middle of a semi-circle of a group of Kaevaphone players (six to eight may be optimum), and is operated by the Director of the Ensemble (the therapy specialist). This Director's Console 202 may be connected to each Kaevaphone 100 by a cable link 204 or a wireless link such as Bluetooth and the like.

With this Console 202 the Director would have many options to coordinate the music of the Ensemble, thereby enhancing the therapeutic effects of our method. These could include but not be limited to:
1) The Tune to be played from a list of Tunes stored by a Processor 206.
2) The speed at which the Tune is to be played.
3) The Mode in which the Tune is to be played.
4) The volume and range of notes for each Kaevaphone.
5) The instrument "sound" to be generated by each. For example, one could be a bass drum, two could be pianos in different octaves, two could sound as flutes, etc.
6) The Console includes a display 208 (preferably a touchscreen) that could scroll through the various functions above and/or also includes control buttons/keyboard 210 so the Director could also generate tones or compose Tunes to be stored by the console processor 206.

Learning Mode

It's probable that these instruments will spend most of their time being played in the "Learning Mode", so some of the options that could be available to this mode could include:
1) The simplest Tunes could be selected for initial learning sessions, such as "Mary Had a Little Lamb", or "Twinkle Twinkle Little Star", etc.
2) The tempo of the selected Tune could be slowed to meet the learning speed of the group of Players.
3) Different "instruments" could be assigned to different Players, so that a Bass Drum could be assigned to a beginner while a piano could be assigned to a more advanced Player.
4) As mentioned above, at each Kaevaphone, the sequence of notes to be played could be lighted on the Tone-Bars in the order to be played. As the Player strikes a lighted Bar; its light would go off; and the next would turn on.

Although the invention has been illustrated and described in detail in the drawings and foregoing description, the same is to be considered as illustrative and not restrictive in character—it being understood that the embodiments shown and described have been selected as representative examples including presently preferred embodiments plus others indicative of the nature of changes and modifications that come within the spirit of the invention(s) being disclosed and within the scope of invention(s) as claimed in this and any other applications that incorporate relevant portions of the present disclosure for support of those claims. Undoubtedly, other "variations" based on the teachings set forth herein will occur to one having ordinary skill in the art to which the present invention most nearly pertains, and such variations are intended to be within the scope of the present disclosure and of any claims to invention supported by said disclosure.

What is claimed is:

1. A dementia therapy method utilizing procedural memory, the method comprising:
    adapting a musical instrument for playing by persons with dementia, the adapted musical instrument comprising:
        one to thirteen tone bars that are sized sufficiently large for easy striking and arranged on a playing surface, and a programmably assignable musical note or percussive beat sound that is generated in response to striking the tone bar by hand or mallet;
    providing one of the adapted musical instruments to each one of a plurality of said persons being designated as players in a musical ensemble;
    determining a level of a player's instrument playing ability by testing the player's use of hand and mallet in striking one or more tone bars in patterns of increasing difficulty;
    programming each player's musical instrument to enable playing a tune component that is designed according to the player's playing ability; wherein the tune component is a set of one or more musical note or rhythmic beat sounds in a pattern that fits at least a portion of the notes and beats of a tune;
    training each player by repetitive practice on their programmed musical instrument; and
    coordinating playing of the musical instruments by the plurality of players combining their respective tune components into a complete tune performed as an ensemble;
    thereby enabling each player to gain self esteem from contributing according to ability to a pleasant sounding musical performance.

2. The dementia therapy method of claim 1, wherein:
    the musical instrument is further adapted for playing by persons having age-related physical limitations, the adaptations comprising:
    a thick handled mallet for easy gripping; and
    the playing surface having an adjustable height and tilt angle for enabling a standing or sitting player to strike the tone bars without raising upper arms.

3. The dementia therapy method of claim 1, wherein levels of instrument playing ability comprise:
    touching a tone bar with a hand, running hands over tone bars, striking a tone bar with a mallet, running the mallet over tone bars, using one mallet to strike with a steady beat, using one mallet to strike with a repeated pattern between two bars, using two mallets to strike with a steady beat, using one or two mallets to strike with a repeated pattern among a plurality of tone bars, and additional levels up to playing a complete tune on a plurality of tone bars.

4. The dementia therapy method of claim 1, wherein musical instrument programming according to instrument playing ability comprises programming the instrument's tone bars to generate:

a selected quantity and range of different sounds;
sounds of a selected musical or rhythm instrument type;
sounds at a selected volume level;
a selected sound assigned to a tone bar in a location on the playing surface selected according to playing ability; and
no sound from optionally selected ones of the tone bars;
wherein selections are made according to a player's playing ability.

5. The dementia therapy method of claim 1, wherein playing coordination comprises determination of:
a tune with a difficulty level that allows design of tune components according to the playing ability of every one of the plurality of players;
playing tempo;
quantity and range of different sounds generated by each player's instrument;
type of musical instrument being simulated by each player's instrument;
volume level of sounds generated by each player's instrument;
selected tone bars to be silenced on any of the players' instruments; and
tune components that will be played by a director or skilled player added to the ensemble.

6. The dementia therapy method of claim 1, further comprising:
a control console connected for programming the tone bars of one or more of the assigned musical instruments.

7. The dementia therapy method of claim 1, wherein:
the tone bars are lighted to indicate a note or beat to be played.

8. The dementia therapy method of claim 7, wherein:
for a sequence of note or beat sounds in a tune component, a tone bar for the next sound to be played is lighted, and when struck it is turned off and the next tone bar to be struck is lighted.

9. The dementia therapy method of claim 7, wherein:
a director coordinates the plurality of players by controlling tone bar lighting using a control console connected to the plurality of players' musical instruments.

10. The dementia therapy method of claim 9, wherein:
the control console comprises a processor for controlling tone bar lighting for the tune components being simultaneously played on the plurality of players' musical instruments.

11. The dementia therapy method of claim 9, wherein:
the director further coordinates by generating sounds to assist in playing the tune.

12. The dementia therapy method of claim 1, wherein:
the tone bars are round disks.

13. The dementia therapy method of claim 1, wherein:
the tone bars are round disks in an organized layout progressing from larger disks for lower pitched notes to smaller disks for higher pitched notes.

* * * * *